US008338481B2

(12) United States Patent
Kloog et al.

(10) Patent No.: US 8,338,481 B2
(45) Date of Patent: Dec. 25, 2012

(54) ALKOXYALKYL S-PRENYLTHIOSALICYLATES FOR TREATMENT OF CANCER

(75) Inventors: Yoel Kloog, Herzliya (IL); Liat Goldberg, Givataim (IL); Victor J. Bauer, Bridgewater, NJ (US)

(73) Assignees: Ramot at Tel-Aviv University Ltd. (IL); Kadmon Corporation, LLC, New York, NY (US)

( * ) Notice: Subject to any disclaimer, the term of this patent is extended or adjusted under 35 U.S.C. 154(b) by 66 days.

(21) Appl. No.: 12/690,174

(22) Filed: Jan. 20, 2010

(65) Prior Publication Data
US 2010/0189781 A1 Jul. 29, 2010

Related U.S. Application Data

(60) Provisional application No. 61/206,108, filed on Jan. 28, 2009.

(51) Int. Cl.
| | |
|---|---|
| *A61K 51/12* | (2006.01) |
| *A61K 9/48* | (2006.01) |
| *A61K 31/03* | (2006.01) |
| *A61K 31/035* | (2006.01) |
| *A61K 31/08* | (2006.01) |
| *A61K 31/095* | (2006.01) |
| *A61K 31/216* | (2006.01) |
| *A61K 31/235* | (2006.01) |

(52) U.S. Cl. ......... 514/546; 514/706; 514/722; 424/456
(58) Field of Classification Search .................. None
See application file for complete search history.

(56) References Cited

OTHER PUBLICATIONS

Goldberg et al. (Journal of Medicinal Chemistry, vol. 52, No. 1, pp. 197-205, Published on Web Dec. 15, 2011).*
Aharonson et al. (Biochimica et Biophysica Acta, vol. 1406, Issue 1, pp. 40-50, Published 1998).*
Remington's Pharmaceutical Sciences Eighteenth Edition, Chapter 89, p. 1662, Published 1990.*
Aharonson et al., "Stringent structural requirements for anti-Ras activity of S-prenyl analogues", Biochimica et Biophysica Acta 1406 (1998), 40-50.
Rotblat et al., "Galectin-1(L11A) Predicted from a Computed Galectin-1 Farnesyl-Binding Pocket Selectively Inhibits Ras-GTP", Cancer Research, vol. 64, 3112-3118, May 1, 2004.
Hancock et al., "All ras proteins are polyisoprenylated by only some are palmitoylated", Cell, vol. 57, 116-1177, Jun. 30, 1989.
Cox et al., "Protein prenylation: more than just glue?", Current Opinion in Cell Biology 1992, 4:1008-1016.
Marciano et al., "Farnesyl Derivatives of rigid carboxylic acids-inhibitors of ras-dependent cell growth", Journal of Medicinal, 1985, 38, 1267-1272.
Cox et al., "Specific isoprenoid modification is required for function of normal, but not oncogenic, ras protein", Molecular and Cellular biology, Jun. 1992, vol. 12, No. 6, p. 2606-2615.
Shohami et al., "The Ras Inhibitor S-trans, trans-Farnesylthiosalicylic Acid Exerts Long-Lasting Neuroprotection in a Mouse Closed Head Injury Model", Journal of Cerebral Blood Flow & Metabolism, 2003, vol. 23, No. 6, 728-738.
Hancock et al., "A CAAX or a CAAL motif and a second signal are sufficient for plasma membrane targeting or ras proteins", The EMBO Journal, 1991, vol. 10 No. 13, pp. 4033-4039.
Elad-Stadia et al., "Galectin-3 Augments K-Ras Activiation and Triggers a Ras Signal That Attenuates ERK but not Phosphoinositide 3-Kinase Activity", The Journal of Biologicl Chemistry, vol. 279, No. 23, Issue of Aug. 13, 2004, pp. 34922-34930.
Elad-Sfadiat et al., "Galectin-1 Augments Ras Activation and Diverts Ras Signals to Raf-1 at the Expense of Phosphoinositide 3-Kinase", The Journal of Biological Chemistry, vol. 277, No. 40, Issue of Oct. 4, 2002, pp. 37169-37175.

* cited by examiner

*Primary Examiner* — Richard Schnizer
*Assistant Examiner* — Alma Pipic
(74) *Attorney, Agent, or Firm* — Lerner, David, Littenberg, Krumholz & Mentlik, LLP

(57) ABSTRACT

Disclosed are alkoxyalkyl S-prenylthiosalicylates and pharmaceutical compositions containing the same and a pharmaceutically acceptable carrier. Methods for treating a human afflicted with cancer, including solid tumors, or a hematological malignancy by administering to the human in need thereof an effective amount of an alkoxyalkyl S-prenylthiosalicylate are also disclosed.

26 Claims, 2 Drawing Sheets

ALKOXYALKYL S-PRENYLTHIOSALICYLATES FOR TREATMENT OF CANCER

CROSS-REFERENCE TO RELATED APPLICATIONS

This application claims the benefit of the filing date of U.S. Provisional Patent Application No. 61/206,108, filed Jan. 28, 2009, the disclosure of which is hereby incorporated herein by reference.

BACKGROUND OF THE INVENTION

Chronically active Ras plays a major role in tumor progression and maintenance in many types of human cancer and, thus, has been a subject of numerous efforts at directed therapy. One such Ras-directed drug is the specific inhibitor S-trans, trans-farnesylthiosalicylic acid (FTS, salirasib) which was designed to mimic the C-terminal farnesyl cysteine carboxymethyl ester of Ras. [Marciano, D., Ben-Baruch, G., Marom, M., Egozi, Y., Haklai, R., and Kloog, Y., J. Med Chem 38:1267-1272 (1995)]. FTS interferes with Ras membrane interactions which are crucial for Ras-dependent cell transformation and tumor growth. [Haklai, R., Gana-Weisz, M., Elad, G., Paz, A., Marciano, D., Egozi, Y., Ben-Baruch, G., and Kloog, Y, Biochemistry 37:1306-1314 (1998)].

SUMMARY OF THE INVENTION

A first aspect of the present invention is directed to an alkoxyalkyl S-prenylthiosalicylate of formula I:

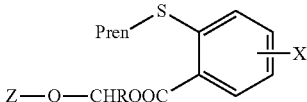

wherein
  Pren represents farnesyl or geranylgeranyl;
  X represents H, F, or Cl;
  R represents H, or alkyl; and
  Z represents alkyl.

Another aspect of the present invention is directed to a method of treating a human afflicted with cancer. The method comprises administering to a human in need thereof an effective amount of an alkoxyalkyl S-prenylthiosalicylate. In some embodiments the cancer is a solid tumor. In another embodiment, the cancer is a hematological malignancy. In yet another embodiment, the alkoxyalkyl S-prenylthiosalicylate administered to the human in need thereof is methoxymethyl S-farnesylthiosalicylate, methoxymethyl S-geranylgeranylthiosalicylate, methoxymethyl 5-fluoro-S-farnesylthiosalicylate, or ethoxymethyl S-farnesylthiosalicylate.

The compound is typically administered in the form of a composition, which is formulated with at least one pharmaceutically acceptable inert ingredient (e.g., a carrier, vehicle, etc.). Modes of administration include oral and intravenous protocols.

A further aspect of the present invention is directed to a pharmaceutical composition. The composition comprises an effective amount of an alkoxyalkyl S-prenylthiosalicylate and a carrier. Methods of making the compositions are further provided.

DETAILED DESCRIPTION

Figure 1:
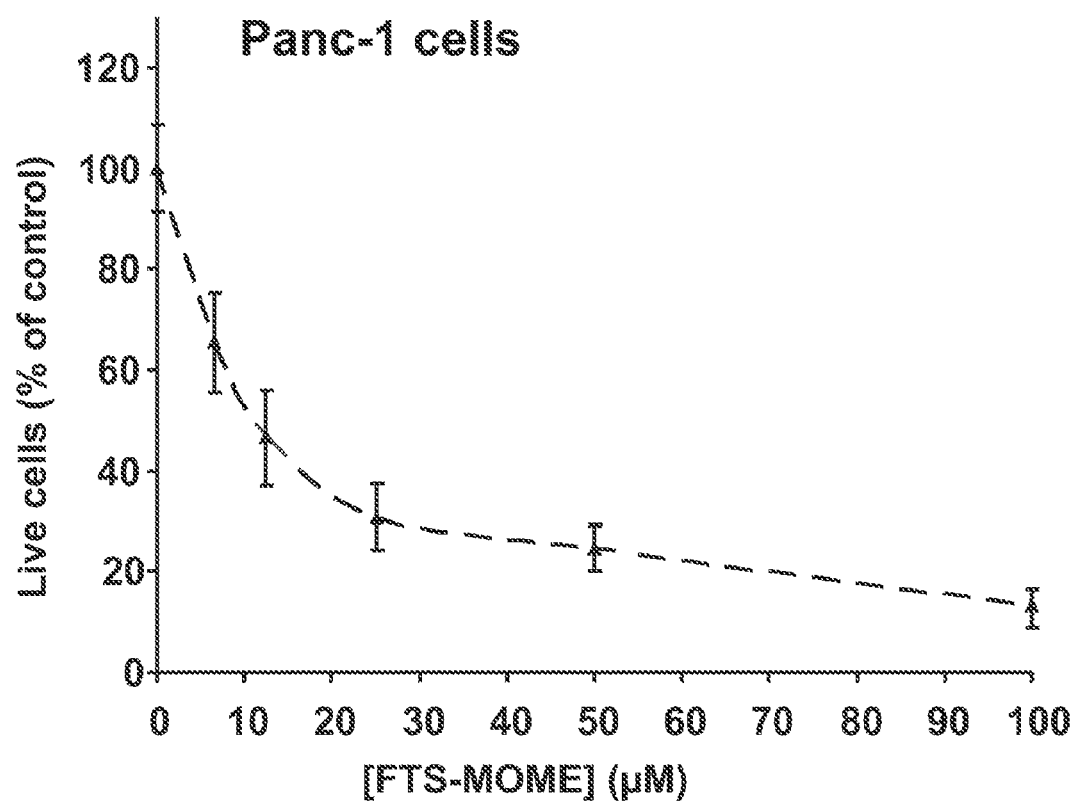
FIG. 1 is a graph showing a dose response curve of inhibition of growth of Panc-1 cells (human pancreatic carcinoma cell line) at increasing concentration of FTS-methoxymethylester (FTS-MOME) (µM), expressed as a percentage of control.

FTS is represented by the formula:

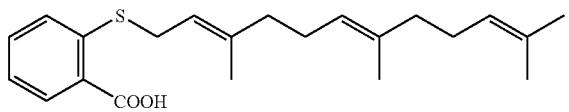

Specific modifications of the FTS carboxyl group by alkoxyalkyl esterification with labile alkoxyalkyl moieties yield active compounds capable of inhibiting cancer cell growth. The esterified FTS derivatives useful in the present invention are alkoxyalkyl S-prenylthiosalicylates represented by formula I:

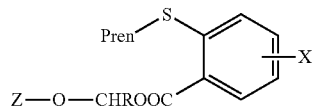

wherein
  Pren represents farnesyl or geranylgeranyl;
  X represents H, F, or Cl;
  R represents H, or alkyl; and
  Z represents alkyl.

In the context of the present invention, "alkyl" refers to any alkyl group of 1 to 20 carbon atoms, linear or branched, substituted or not substituted, and saturated or unsaturated. In some embodiments, "alkyl" refers to an alkyl group of 1 to 4 carbon atoms (i.e., a lower C1 to C4 alkyl) which may be linear or branched (e.g., methyl, ethyl, n-propyl, i-propyl, n-butyl, i-butyl, and/or t-butyl).

The alkoxyalkyl S-prenylthiosalicylates embraced by formula I include, for example, methoxymethyl S-farnesylthiosalicylate, methoxymethyl S-geranylgeranylthiosalicylate, methoxymethyl 5-fluoro-5-farnesylthiosalicylate, and ethoxymethyl S-farnesylthiosalicylate. Structures of these compounds are set forth below.

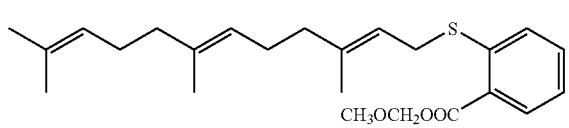

methoxymethyl S-farnesylthiosalicylate;

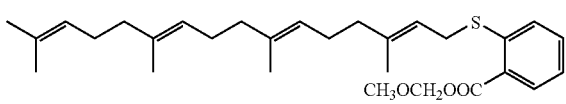

methoxymethyl S-geranylgeranylthiosalicylate;

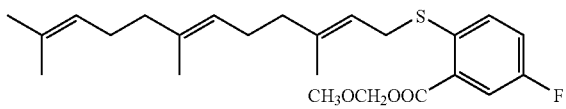

methoxymethyl 5-fluoro-5-farnesylthiosalicylate;

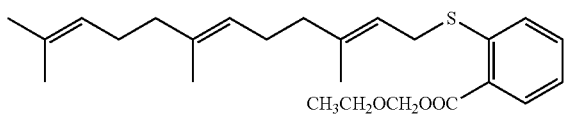

ethoxymethyl S-farnesylthiosalicylate.

The compositions of the present invention are useful in treating diseases and disorders responsive to the Ras antagonists of formula I, e.g., diseases and disorders characterized or mediated, at least in part, by abnormal (e.g., uncontrolled) cell proliferation, such as Ras-induced cell proliferation. Of course, the term "responsive" does not require that a therapeutic response would be achieved in each and every patient, but rather what a skilled practitioner would reasonably expect based on existing data from patient populations. These diseases and disorders include cancers, such as cancers involving solid tumors and hematological malignancies, which generally do not form solid tumors. In some embodiments, the solid tumors treatable in accordance with the present invention include, for example, pancreatic tumors, lung tumors, tumors of the colon, breast tumors, ovarian tumors, prostate tumors, melanomas, and brain tumors, including glioblastomas and brain metastases of primary tumors. In some embodiments, the hematological malignancies treatable in accordance with the present invention include myelodysplastic syndrome and leukemias, including acute myeloid leukemia.

The frequency of administration, dosage amounts, and the duration of treatment of each of the active agents may be determined depending on several factors which may include the overall health, size and weight of the patient, the severity and type of the cancer, the patient's tolerance to the treatment, and the particular treatment regimen being administered. For example, duration of treatment with the alkoxyalkyl S-prenylthiosalicylates may last a day, a week, a year, or until remission of the cancer is achieved.

As used herein, the term "effective amount" refers to the dosage(s) of alkoxyalkyl S-prenylthiosalicylates that is effective for prophylaxis and for treating, and thus includes dosage amounts that inhibit or reduce the likelihood or onset of cancer, or amounts that ameliorate existing cancer and its associated manifestations, or delay or slow injury progression, or prolong patient survival. The average daily dose of alkoxyalkyl S-prenylthiosalicylates generally ranges from about 50 mg to about 2000 mg, and in some embodiments, from about 200 mg to about 1600 mg.

In some embodiments, the composition is administered on a daily basis, e.g., in a single once-a-day or divided doses. In other embodiments, the composition is administered two or more times per day.

The methods and compositions of the present invention may be used for the treatment of cancer in mammals, particularly humans. The active pharmaceutical ingredients may be administered in accordance with standard methods. In preferred embodiments, the composition is administered orally. Accordingly, alkoxyalkyl S-prenylthiosalicylates may be administered by dosing orally daily, or by dosing for three weeks with a one-week "off period" and repeating until remission is achieved. In an oral dosage form, the alkoxyalkyl S-prenylthiosalicylate is typically present in a range of about 100 mg to about 500 mg, and in some embodiments, the alkoxyalkyl S-prenylthiosalicylate ranges from about 100 mg to about 300 mg.

Administration of alkoxyalkyl S-prenylthiosalicylates may be cyclic and repeated until remission is achieved. For example, in one treatment regimen, the Ras antagonist is administered according to the following schedule: (1) administering daily for a period of three weeks followed by a one-week interval without active pharmaceutical ingredient ("off period"); and (2) repeating step (1) as many times as needed, e.g., until remission or stable disease is achieved. Under this regimen, the active pharmaceutical ingredient is administered in a three-week cycle separated by a one-week off period. In another embodiment, step (1) further includes oral dosing with the composition for an additional week (four weeks) followed by a one-week "off period" before repeating step (1).

Oral compositions for alkoxyalkyl S-prenylthiosalicylates for use in the present invention can be prepared by bringing the agent(s) into association with (e.g., mixing with) a pharmaceutically acceptable carrier. Suitable carriers are selected based in part on the mode of administration. Carriers are generally solid or liquid. In preferred embodiments, compositions may contain liquid carriers. Compositions suitable for oral administration that contain the active are preferably in dosage forms such as soft gelatin capsules. The compositions, however, may be contained in other carriers that enable administration to a patient in other oral forms, e.g., a liquid or gel. Regardless of the form, the composition is divided into individual or combined doses containing predetermined quantities of the active ingredient or ingredients.

In a preferred embodiment, an alkoxyalkyl S-prenylthiosalicylate of the invention is formulated as a soft-gelatin capsule. The alkoxyalkyl S-prenylthiosalicylate is dissolved in a pharmaceutically acceptable liquid carrier such as a vegetable oil (corn oil, coconut oil, for example), a fatty alcohol (stearyl alcohol, myristyl alcohol, for example), a glyceride (glycerol stearate, glycerol monooleate, for example), or a polyvinyl alcohol (PEG4000, for example), or mixtures thereof. The liquid carrier may also contain an emulsifying agent (polysorbate 80, lecithin, for example). The resulting solution is formed into soft-gelatin capsules with a soft-gelatin encapsulating machine.

The compounds of this invention can be synthesized by reacting under anhydrous conditions, in a suitable unreactive solvent, a salt (e.g., the sodium salt) of an S-prenylthiosalicylic acid with an alkoxyalkylhalide (e.g., chloride or bromide) for a sufficient period of time at a suitable temperature to effect conversion of the reactants to an alkoxyalkyl S-prenylthiosalicylate. Persons skilled in the art may determine which salts of S-prenylthiosalicylic acid react best with the alkoxyalkylhalide under the prescribed conditions set forth in the examples section. Persons skilled in the art will appreciate that the adjustments of other parameters associated with the synthesis of alkoxyalkyl S-prenylthiosalicylates (e.g., time and temperature) may also have a positive effect on the resulting compound and its synthesis.

In order to fully illustrate the present invention and advantages thereof, the following specific examples/experiments are given, it being understood that the same is intended only as illustrative and in no way limitative.

Example 1

Experimental Design

The purpose of the following experiments was to determine whether specific modifications of the FTS carboxyl group yielded active compounds that inhibited growth of human cancer cell lines. A first set of experiments was performed in vitro using the human pancreatic carcinoma cell line panc-1, which is a common cell line used for investigating the treatment of pancreatic cancer. A second set of experiments were performed in vitro using the human glioblastoma cell line U-87, which is a common cell line used for investigating the treatment of brain tumors. Glioblastoma is the highest dedifferentiated form of astrocytic brain tumor, and it is refractory to chemotherapy in most cases. U-87 (malignant glioma) cells are commonly used as an in vitro model to investigate the cytotoxic effect of chemotherapeutic drugs towards cancer cells.

The results indicated that specific modifications of the FTS carboxyl group by conversion of FTS to its methoxymethylene ester caused improved potency as compared to FTS in inhibiting tumor cell growth in Panc-1 and U-87 human cell lines. Specifically, FTS-MOME demonstrated growth inhibitory effects in both Panc-1 and U-87 cell lines with an $IC_{50}$ (concentration of FTS-MOME causing 50% inhibition of cell growth) of 15 µM in both cell lines.

Materials and Methods
Synthesis of Methoxymethyl S-Farnesylthiosalicylate

While stirring, 1 ml hexamethylphosphoramide was added to a flask containing 0.264 grams sodium hydride under argon. With cooling, a solution of 3.59 S-trans, trans-farnesylthiosalicylic acid (FTS) [Concordia Pharmaceuticals, Inc.] in 10 ml hexamethylphosphoramide was added dropwise over 30 minutes. The mixture was then stirred at room temperature for 30 minutes. In one portion, 0.84 ml chloromethyl methyl ether was added and stirring was continued for 3 hours. The mixture was poured into saturated aqueous sodium carbonate, and extracted with ether. The ether solution was washed with water and brine, dried over sodium sulfate, and concentrated to an oil, which was chromatographed on a filterpad of flash silica, eluting with hexanes/ethyl acetate (20/1) to provide 3.1 g (78%) of colorless oil, purity≈99%.

1H-NMR (300 MHz, CDCl$_3$) δ: 8.03 (dd, 1H), 7.45 (t, 1H), 7.33 (d, 1H), 7.17 (td, 1H), 5.49 (s, 2H), 5.34 (bt, 1H), 5.09 (bt, 2H), 3.59 (d, 2H), 3.56 (s, 3H), 2.1-2.0 (m, 6H), 1.99-1.96 (m, 2H), 1.73 (s, 3H), 1.68 (s, 3H), 1.59 (s, 6H). LC/MS (+)ESI: m/z 425 [M+Na]+

Inhibition of Panc-1 Cell Growth by Methoxymethyl S-Farnesylthiosalicylate

Human pancreatic cancer Panc-1 cells were obtained from American Tissue Culture Collection (ATCC) and grown in Dulbecco's modified Eagle medium (DMDM) containing 10% fetal calf serum, 2 mM L-glutamine, 100 U/mL penicillin, and 100 µg/mL streptomycin. The cells were incubated at 37° C. in a humidified atmosphere of 95% air and 5% $CO_2$. Cells were plated in 24-well plates at a density of 5000 cells per well and grown for 24 hours. The medium was then replaced by a medium containing the desired concentration of methoxymethyl S-farnesylthiosalicylic acid and 0.1% DMSO, or by a medium containing 0.1% DMSO (control). Cells were maintained in culture for 5-7 days and then counted. Data are expressed as a percentage: (number cells in drug-treated culture/number cells in control culture×100). Experiments were performed twice in quadruplicates and means±SD are represented graphically in FIG. 1.

Inhibition of U87 Cell Growth by Methoxymethyl S-Farnesylthiosalicylate

Human glioblastoma U87 cells were obtained from American Tissue Culture Collection (ATCC) and grown in Dulbecco's modified Eagle medium (DMDM) containing 10% fetal calf serum, 2 mM L-glutamine, 100 U/mL penicillin, and 100 µg/mL streptomycin. The cells were incubated at 37° C. in a humidified atmosphere of 95% air and 5% $CO_2$. Cells were plated in 24-well plates at a density of 5000 cells per well and grown for 24 hours. The medium was then replaced by a medium containing the desired concentration of methoxymethyl S-farnesylthiosalicylic acid and 0.1% DMSO, or by a medium containing 0.1% DMSO (control). Cells were maintained in culture for 5-7 days and then counted. Data are expressed as a percentage: (number cells in drug treated culture/number cells in control×100). Experiment was performed twice in quadruplicates and means±SD are represented graphically in FIG. 2.

Methoxymethyl S-Farnesylthiosalicylate Soft Gelatin Capsules (200 mg)

Methoxymethyl S-Farnesylthiosalicylate (2.0 kg) is uniformly dispersed in a mixture of corn oil (3.0 kg), lecithin (30 g), and Tween-80 (150 g) and filled into soft gelatin capsules. Assuming a 5% loss on material transfers and soft gelatin encapsulating machine start-up, adjustment, and shut-down, approximately 9,500 methoxymethyl S-farnesylthiosalicylate 200 mg capsules are yielded.

Results
Methoxymethyl S-Farnesylthiosalicylate (FTS-MOME) Inhibits Cancer Cell Growth In Vitro To establish efficacy of the newly synthesized compound FTS-MOME, Applicants prepared cell growth assays using human cancer cell lines. In vitro growth inhibition assays were performed using (1) a cancer cell line that harbors an oncogenic K-Ras, the human pancreatic cancer cell line panc-1, and (2) a cancer cell line in which Ras is not mutated but is chronically active due to high activity of growth factor receptors, the human glioblastoma cell line U-87.

First, to examine the effects of FTS-MOME on panc-1 cell growth (i.e., growth inhibition), the cells were incubated with and without FTS-MOME for five (5) days and the live cells were counted as a percentage of control over concentration of FTS-MOME (µM). The results showed a dose-dependent decrease in live cancer cell number at the concentration range of 6-100 µM with an $IC_{50}$ of 15 µM in panc-1 cells, as illustrated in FIG. 1. The inhibitory effects of FTS-MOME on panc-1 cells was mainly due to inhibition of cell growth, except for the higher dose where cell death was observed as well.

Figure 2:
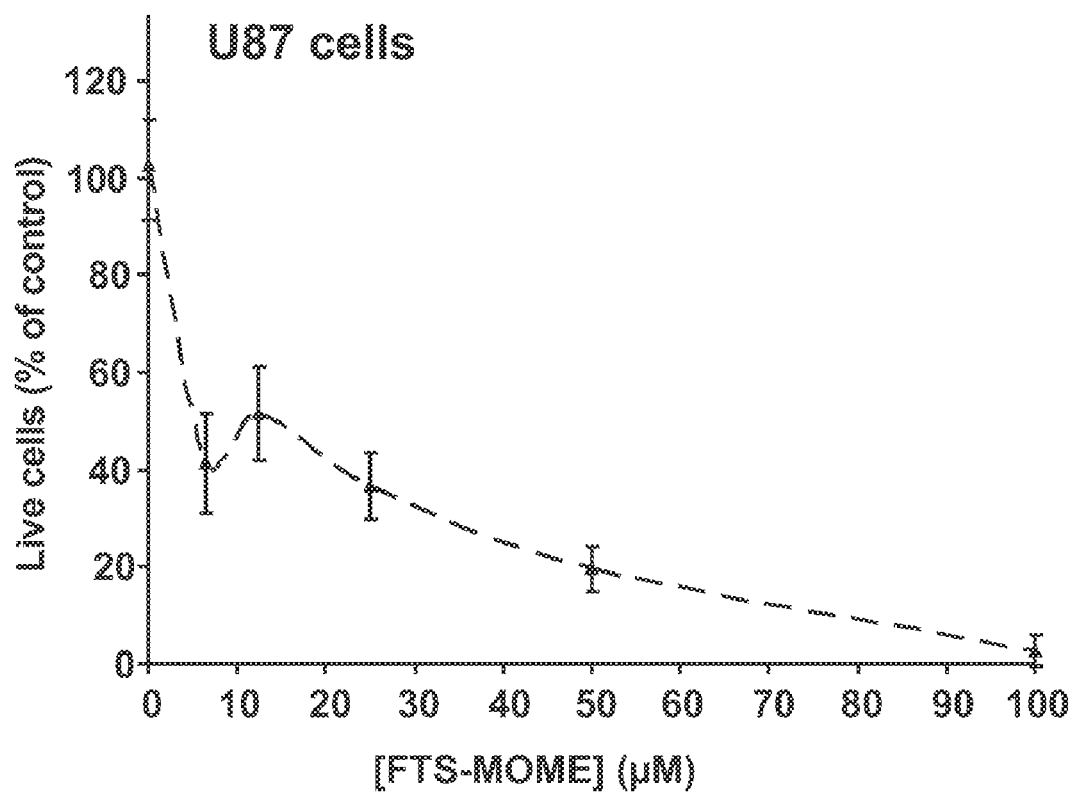
FIG. 2 is a graph showing a dose response curve of inhibition of growth of U87 cells (human glioblastoma-astrocytoma cell line) at increasing concentration of FTS-methoxymethylester (FTS-MOME) (µM), expressed as a percentage of control.

Next, to examine the effects of FTS-MOME on U-87 cell growth (i.e., growth inhibition), the cells were incubated with and without FTS-MOME for five (5) days and the live cells were counted as a percentage of control over concentration of FTS-MOME (µM). Similar to that observed in panc-1 cells, the results showed a dose-dependent decrease in live cancer cell number in U-87 cells at the concentration range of 6-100 µM with an $IC_{50}$ of 15 µM, as illustrated in FIG. 2. The inhibitory effects of FTS-MOME on U-87 cells was mainly due to inhibition of cell growth, except for the higher dose where cell death was observed as well.

Taken together, these results demonstrate that certain modifications of the carboxyl group of FTS yield an active compound capable of inhibiting cancer cell growth. The $IC_{50}$ of growth inhibition for FTS was previously determined to be 35 μM for panc-1 cells [Weisz, B., Giehl, K., Gana-Weisz, M., Egozi, Y., Ben-Baruch, G., Marciano, D., Gierschik, P., and Kloog, Y., Oncogene 18: 2579-2588 (1999)] and 50 μM for U-87 cells [Blum, R., Jacob-Hirsch, J., Amariglio, M., Rechavi, G., and Kloog, Y., Cancer Research 65: 1-8 (2005)]. Thus, conversion of FTS to its methoxymethylene ester improved potency as compared to FTS in inhibiting tumor cell growth.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound of the formula:

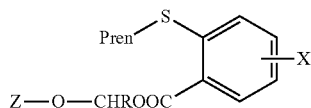

wherein
Pren is farnesyl or geranylgeranyl;
X is H, F, or Cl;
R is H, or alkyl; and
Z is alkyl.

2. The compound of claim 1, which is methoxymethyl S-farnesylthiosalicylate (FTS-MOMS).

3. The compound of claim 1, which is methoxymethyl S-geranylgeranylthiosalicylate.

4. The compound of claim 1, which is methoxymethyl 5-fluoro-S-farnesylthiosalicylate.

5. The compound of claim 1, which is ethoxymethyl S-farnesylthiosalicylate.

6. A method of treating a human afflicted with cancer, comprising administering to the human in need thereof an effective amount of a compound having the formula:

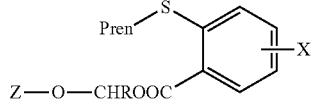

wherein
Pren is farnesyl or geranylgeranyl;
X is H, F, or Cl;
R is H, or alkyl; and
Z is alkyl.

7. The method of claim 6, wherein the human is administered methoxymethyl S-farnesylthiosalicylate (FTS-MOMS).

8. The method of claim 6, wherein the human is administered methoxymethyl S-geranylgeranylthiosalicylate.

9. The method of claim 6, wherein the human is administered methoxymethyl 5-fluoro-S-farnesylthiosalicylate.

10. The method of claim 6, wherein the human is administered ethoxymethyl S-farnesylthiosalicylate.

11. The method of claim 6, wherein the cancer is a solid tumor.

12. The method of claim 11, wherein the solid tumor is a pancreatic tumor.

13. The method of claim 11, wherein the solid tumor is a lung tumor.

14. The method of claim 11, wherein the solid tumor is a colon cancer.

15. The method of claim 11, wherein the solid tumor is a glioblastoma.

16. The method of claim 11, wherein the solid tumor is a brain metastasis of a primary tumor.

17. The method of claim 11, wherein the solid tumor is a breast tumor.

18. The method of claim 11, wherein the solid tumor is an ovarian tumor.

19. The method of claim 11, wherein the solid tumor is a prostate tumor.

20. The method of claim 11, wherein the solid tumor is a melanoma.

21. The method of claim 6, wherein the cancer is a hematological malignancy.

22. The method of claim 21, wherein the hematological malignancy is myelodysplastic syndrome.

23. The method of claim 21, wherein the hematological malignancy is acute myeloid leukemia (AML).

24. A pharmaceutical composition comprising an effective amount of the compound of the formula:

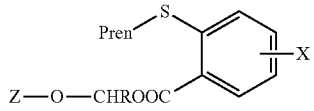

wherein
Pren is farnesyl or geranylgeranyl;
X is H, F, or Cl;
R is H, or alkyl; and
Z is alkyl; and
a pharmaceutically acceptable carrier.

25. The composition of claim 24, which is in the form of a soft gelatin capsule.

26. The composition of claim 24, which is methoxymethyl S-farnesylthiosalicylate; and which is in the form of a soft gelatin capsule.

* * * * *

UNITED STATES PATENT AND TRADEMARK OFFICE
CERTIFICATE OF CORRECTION

| | | |
|---|---|---|
| PATENT NO. | : 8,338,481 B2 | Page 1 of 1 |
| APPLICATION NO. | : 12/690174 | |
| DATED | : December 25, 2012 | |
| INVENTOR(S) | : Yoel Kloog et al. | |

It is certified that error appears in the above-identified patent and that said Letters Patent is hereby corrected as shown below:

In the Claims

Column 7, line 35, "MOMS" should read -- MOME --.
Column 8, line 3, "MOMS" should read -- MOME --.

Signed and Sealed this
Second Day of September, 2014

Michelle K. Lee
*Deputy Director of the United States Patent and Trademark Office*